June 26, 1973 W. E. DUFFETT ET AL Plant Pat. 3,367
CARNATION PLANT
Filed Nov. 29, 1971
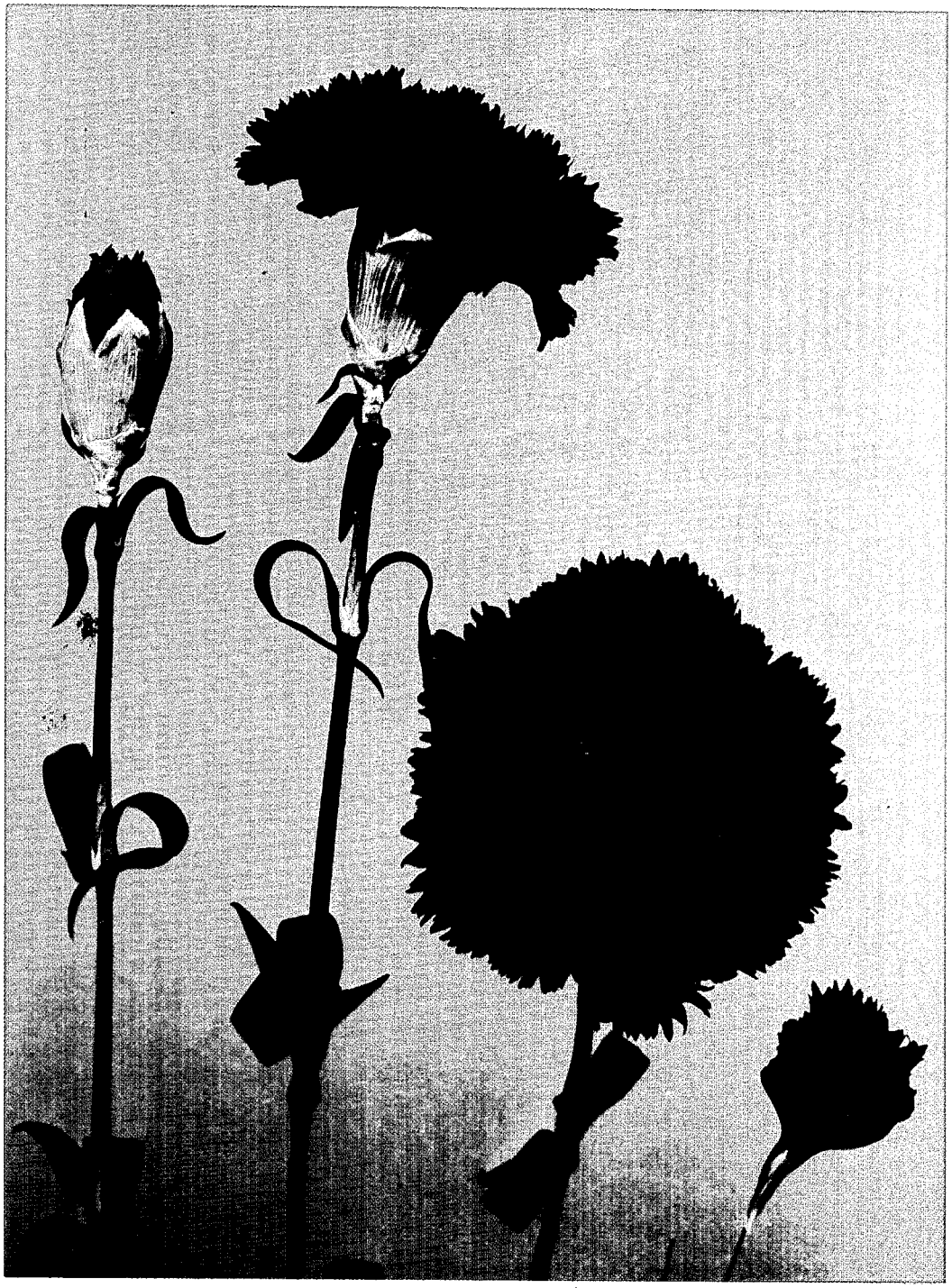

United States Patent Office

Plant Pat. 3,367

Patented June 26, 1973

3,367
CARNATION PLANT

William E. Duffett, Akron, Ohio, and Thomas G. Harcharick, Salinas, Calif., assignors to Yoder Brothers, Inc., Barberton, Ohio

Filed Nov. 29, 1971, Ser. No. 203,087
Int. Cl. A01h *5/00*
U.S. Cl. Plt.—73 1 Claim

The present invention comprises a new and distinct cultivar of carnation plant which is a seedling of #YB 2834 × #YB 2826. Both parents are unpatented and are identified for breeding purposes by the above numbers to distinguish the same from other parents in the breeding program.

The new cultivar is similar in certain respects to the unpatented variety Diplomat, having the same characteristics of:

(1) Closely similar crimson red color.

(2) Year round, perpetual flowering traits.

(3) Suitability to standard or disbud commercial cut flower production.

(4) Foliage size and shape.

The new cultivar is distinguished from Diplomat by the following characteristics, when grown under comparable conditions:

(1) Plant habit is four to six inches shorter.

(2) Stems are stronger and average five inches shorter.

(3) Response or flowering peaks approximately three to four weeks earlier on the first crop from comparative single pinch crops planted and pinched on approximately the same date. The return crop peaks approximately four to six weeks earlier.

(4) Crops of approximately 11 months duration, from plant date to discard date, produce approximately 13 more steps per square foot.

(5) Splitting and slabbing percentages are significantly less.

(6) Flower size is one-quarter to three-quarters of an inch larger in diameter, with approximately 20–30 more petals.

(7) Petal margin is more deeply serrated.

(8) Petals develop less burn or dehydration of the petal margin, which is often observed in Diplomat.

(9) Keeping quality of the flower is approximately three to four days longer.

The new cultivar was selected from the progeny of the designated cross and when asexually reproduced by cuttings at Salinas, Calif., has been found to retain its distinctive characteristics through successive propagations.

The accompanying photographic drawing illustrates the new cultivar, with the color being as nearly true as possible with color illustrations of this type.

The following detailed description is based on observations made of the new cultivar in a greenhouse in Salinas, Calif. The response time, blooming period, total vigor and color may vary significantly with varying environmental conditions such as temperature, day-length and light intensity. In the description, color references are made to the Munsel Color Book, 1963 edition, and comparisons are made with the cultivar Diplomat. Where only a single value or description appears for the new cultivar, the same value or description applies to the comparison cultivar as well.

Botanical classification: *Dianthus carophyllus*

| | Chieftan | Diplomat |
|---|---|---|
| Bloom: | | |
| Type | Disbud | |
| Size | 3¼–3¾ | 2½–3½. |
| Petal edge | Deeply serrated | Serrated. |
| Petal count | 70–76 | 46–48. |
| Petal texture | Smooth | |
| Petal size: | | |
| Average length | 2½″ | 2¼″. |
| Average width | 1½″ | 1¼″. |
| Bud shape | Ovoid | |
| Splitting tendency | Low | Moderate to high. |
| Slab tendency | do | |
| Keeping quality | 8–12 days | 5–8 days. |
| Fragrance | Mild to none | Mild. |
| Color: | | |
| Center of flower | Carmine, 5R3/12 (closest approximation) | Carmine, 5R3/12. |
| Base of petals | Light yellow green, 5GY8/14 | Light yellow green, 2.5GY8/6. |
| Inside of petals | Carmine, 5R3/12 (closest approximation) | Carmine, 5R3/12. |
| Reverse of petals | Crimson, 2.5R3/10 | Crimson, 2.5R3/8. |
| Color stability | Good | |
| Seasonal variations | None | |
| Reproductive organs: | | |
| Stamen, anthers | White N9/ to violet 8.75RP4/12 | White N9/ to violet 10RP3/10. |
| Pollen | Light tan 5Y8/4 | Light tan 5Y8/4. |
| Stigma | 2–3 lobes, white N9/ with violet reverse 8.75RP4/12. | 2–3 lobes, white N9/ with violet reverse 10RP3/10. |
| Styles | 3 lobed, 1.25R4/12 | 3 lobed, white N9/. |
| Length | 1⅛″ | 1⅜″. |
| Ovaries: | | |
| Tip | Greyed yellow, 5Y5/6. | Greyed yellow, 2.5Y7/8. |
| Mid | Yellow green, 2.5GY7/10 | 2.5GY7/8. |
| Base | Ivory, 5Y9/2 | Ivory, 10Y9/1. |
| Calyx: | | |
| Size | 1¼″ | 1⅜″. |
| Shape | Tubular | Tubular. |
| Number of sepals | 5 | 5. |
| Stems: | | |
| Length | 18″–21″ | 23″–26″. |
| Bending traits | 12 o'clock | 1 o'clock. |
| Plant: | | |
| Form | Erect and branching bush | Erect and branching bush. |
| Growth | Vigorous, strong, sturdy, and upright | |
| Height (from a single pinched crop approximately 11 months in duration from plant date to discard date). | 33″ | 38″. |
| Foliage: | | |
| Topside (color) | Dark green, 7,5GY3/4 | |
| Underside (color) | do | |
| Mature (color) | do | |
| Length, mature leaf | 6″ | |
| Shape | Acicular | |
| Texture | Glaucous | |
| Displacement | Opposite | |

TABLE—Continued

| | Chieftan | Diplomat |
|---|---|---|
| Production and grade data comparison from a single planting in Salinas, Calif.: | | |
| Plant date | July 18 | July 25. |
| Pinch date | August 12 | August 15. |
| First cut | November 27 | December 2. |
| Peak flowering | December 16 | January 20. |
| Second crop peaked | April 12 | May 31. |
| Crop weeks | 47 | 47. |
| Flower production per sq. ft | 33.68 | 20.48. |
| Grade data based on Society of American Florists Grade Standard: | | |
| Blue | 12.1% | 25.2%. |
| Red | 46.2% | 41.4%. |
| Green | 29.4% | 10.1%. |
| Splits | 3.3% | 21.3%. |
| Slabs | 4.7% | 1.9%. |
| Unsaleable | 4.1% | 0.0%. |
| Discard date | June 14 | June 21. |

We claim:

1. A new and distinct cultivar of carnation characterized particularly as to its uniqueness when compared to the cultivar Diplomat by its stems which are stronger and average five inches shorter; its response or flowering peaks which are approximately three to four weeks earlier on the first crop from comparative single pinch crops planted and pinched on approximately the same date, with the return crop peaking approximately four to six weeks earlier; by its higher production, producing approximately 13 more stems per square foot from crops of approximately 11 month duration from plant date to discard date; by its splitting and slabbing percentages which are significantly less; by its flower size which is one-quarter to three-quarters of an inch larger in diameter, with approximately 20–30 more petals, with the petal margin being more deeply serrated and developing less burn or dehydration of the petal margin, and by its keeping quality, with the flowers keeping approximately three to four days longer.

No references cited.

ROBERT E. BAGWILL, Primary Examiner

UNITED STATES PATENT OFFICE
CERTIFICATE OF CORRECTION

Patent No. 3,367 Dated June 26, 1973

Inventor(s) WILLIAM E. DUFFETT and THOMAS G. HARCHARIK

It is certified that error appears in the above-identified patent and that said Letters Patent are hereby corrected as shown below:

In column 1, line 4, "Harcharick" should be --Harcharik--.

In column 2, line 3, "steps" should be --stems--.

In the tabulation, about line 46 of same, under "Foliage:" opposite "Topside (color)", "7,5GY3/4" should be --7.5GY3/4--.

Signed and sealed this 1st day of October 1974.

(SEAL)
Attest:

McCOY M. GIBSON JR.
Attesting Officer

C. MASHALL DANN
Commissioner of Patents